US007674949B2

(12) United States Patent
Wahlstrom et al.

(10) Patent No.: US 7,674,949 B2
(45) Date of Patent: Mar. 9, 2010

(54) ABSORBENT ARTICLE COMPRISING A LIQUID TRANSFER LAYER

(75) Inventors: Johan Wahlstrom, Gothenburg (SE);
Bror-Inge Helmfridsson, Partille (SE);
Ken Olsson, Vastra Frolunda (SE);
Patrik Andersson, Gothenburg (SE);
Anne Farbrot, Askim (SE)

(73) Assignee: SCA Hygiene Products AB, Gothenburg (SE)

( * ) Notice: Subject to any disclaimer, the term of this patent is extended or adjusted under 35 U.S.C. 154(b) by 516 days.

(21) Appl. No.: 11/366,602

(22) Filed: Mar. 3, 2006

(65) Prior Publication Data

US 2006/0229579 A1 Oct. 12, 2006

Related U.S. Application Data

(60) Provisional application No. 60/658,206, filed on Mar. 4, 2005.

(51) Int. Cl.
*A61F 13/15* (2006.01)
*A61F 13/20* (2006.01)
(52) U.S. Cl. .............. 604/380; 604/370; 604/385.01; 604/383
(58) Field of Classification Search .......... 604/366, 604/383, 385.01, 365, 385.101, 380, 378
See application file for complete search history.

(56) References Cited

U.S. PATENT DOCUMENTS 3,371,667 A 3/1968 Morse

| 4,781,962 | A | | 11/1988 | Zamarripa et al. |
| 4,908,026 | A | | 3/1990 | Sukiennik et al. |
| 5,188,625 | A | * | 2/1993 | Van Iten et al. ............. 604/383 |
| 5,591,149 | A | | 1/1997 | Cree et al. |
| 5,613,960 | A | | 3/1997 | Mizutani |
| 6,916,969 | B1 | * | 7/2005 | Helmfridsson et al. ...... 604/378 |

FOREIGN PATENT DOCUMENTS

| EP | 0 312 118 A2 | 4/1989 |
| EP | 0 474 777 B1 | 3/1992 |

(Continued)

OTHER PUBLICATIONS

Notice of Reasons for Rejection mailed Oct. 6, 2009 in corresponding Application No. JP 2007-557000.

*Primary Examiner*—Michele Kidwell
(74) *Attorney, Agent, or Firm*—Buchanan Ingersoll & Rooney PC

(57) ABSTRACT absorbent article comprising a liquid transfer layer (5) positioned between a liquid pervious bodyside liner (6) and an absorbent core (2). The liner (6) comprises a plurality of perforations (7). The liner and the transfer layer are bonded together in a plurality of bonding sites (11) covering an area of between 0.5% and 11% of the area of the liner (6) that is circumscribed by the bonding sites and wherein each bonding site has an area of no more than 13 mm². The combined perforated liner (6) and transfer layer (5) provides a quick inlet of liquid and a low rewet against the wearer. The liner (6) has a three-dimensional structure of alternating raised and depressed regions and the perforations (7) are present in the bottoms of the depressions (8) of said liner as seen from the body facing side of the liner.

16 Claims, 8 Drawing Sheets

FOREIGN PATENT DOCUMENTS

| | | | |
|---|---|---|---|
| GB | 2 235 878 A * | 3/1991 | |
| GB | 2 335 627 A * | 9/1999 | |
| JP | 63-267359 | 11/1988 | |
| JP | 2002-165830 | 6/2002 | |
| JP | 2004-000465 | 1/2004 | |
| WO | WO 93/11725 A1 * | 6/1993 | |
| WO | WO 97/02133 A2 * | 6/1996 | |
| WO | 96/40513 | 12/1996 | |
| WO | 97/02133 | 1/1997 | |
| WO | 99/14415 | 3/1999 | |
| WO | 99/49825 | 10/1999 | |
| WO | 00/02727 | 1/2000 | |
| WO | WO 00/19957 A1 * | 4/2000 | |
| WO | 00/37249 | 6/2000 | |
| WO | WO 01/03626 A1 * | 1/2001 | |

* cited by examiner

ABSORBENT ARTICLE COMPRISING A LIQUID TRANSFER LAYER

TECHNICAL FIELD

The present invention refers to an absorbent article comprising a liquid transfer layer positioned between a liquid pervious bodyside liner and an absorbent core. The absorbent article can be a diaper, a pant diaper, a sanitary napkin, a pantyliner, an incontinence guard or the like.

BACKGROUND OF THE INVENTION

Absorbent articles of the above mentioned kind are intended to absorb body liquids such as urine and blood. They usually comprise a liquid pervious bodyside liner, intended to be facing the wearer during use. The liner may be a nonwoven material, an apertured plastic film or a laminate of a nonwoven material and an apertured film. It is known to incorporate a liquid transfer layer between the liner and the absorbent core, said liquid transfer layer having the ability to quickly receive large amounts of liquid, to distribute it and temporarily store it before it is absorbed by the underlying absorbent core. This is important especially in today's thin compressed absorbent bodies often with a high amount of so called superabsorbents, which have a high liquid absorption and storage capacity but in many cases a too low absorption speed in order to momentaneously be able to absorb the large amount of liquid that can be discharged during a few seconds at urination.

A porous relatively thick liquid transfer layer, for example in the form of a fibrous wadding, a carded fibrous web or other type of fibrous material, has a high momentaneous liquid receiving capacity and can temporarily store liquid before it is absorbed by the absorbent body. The same applies for porous foam materials. The liquid is then drained successively to the underlying absorbent core, after which the transfer layer again has capacity to receive liquid from a repeated wetting.

Examples of absorbent articles comprising such porous liquid transfer layer are for example disclosed in U.S. Pat. No. 3,371,667, EP-A-0,312,118 and EP-A-0,474,777.

U.S. Pat. No. 4,908,026 discloses an absorbent article having a liquid pervious liner containing a plurality of perforations. The article further contains a flow zone control layer arranged between the perforated liner and the absorbent core.

WO 99/49825 discloses a material laminate for use as an outer liner on an absorbent article. The laminate comprises a first liquid pervious fibrous material layer and a second porous and resilient material layer, wherein the two material layers have been fused together in a pattern of bonding sites.

U.S. Pat. No. 5,613,960 discloses a fibrous liquid transfer layer disposed between the topsheet and the absorbent core, and wherein the liquid transfer layer is intermittently fused to the topsheet in a direction of thickness to improve fluid flow into the core.

WO 97/02133 discloses a laminate comprising an apertured film and a compressible material in the form of a nonwoven. The film and the nonwoven layer are bonded together to form a series of valleys and peaks.

WO 00/37249 discloses a composite laminate web comprising a first layer in the form of an apertured nonwoven and a second layer in the form of an apertured film, which are bonded together.

WO 96/40513 discloses a laminate comprising a first film layer and a second fibrous layer bonded together in a spaced apart bonding pattern. Apertures are formed in the bonded areas.

U.S. Pat. No. 5,591,149 discloses a laminate in the form of an apertured film that is fused to an acquisition web at discrete points of attachment.

U.S. Pat. No. 4,781,962 discloses a laminate comprising a perforated film an a nonwoven which is fused to the film in the areas of the perforations, so as to mask and restrict fluid flow through the perforations.

A problem that may occur is that conventional bodyside liner materials used for absorbent articles sometimes have a lower acquisition rate for liquid than the liquid transfer layer, at which liquid can leak out from the article before it reaches the liquid transfer layer. Another problem is that liquid that has been absorbed by the liquid transfer layer may leak out again through the liner and cause so called rewet and a wet feel to the wearer. The interaction between the bodyside liner and the liquid transfer layer is therefore of importance in order to quickly absorb the discharged liquid and to prevent rewet and provide a dry surface to the wearer.

OBJECT AND MOST IMPORTANT FEATURES OF THE INVENTION

An object of the present invention is to provide an absorbent article having a bodyside liner and a liquid transfer layer which interact in such a way that a rapid liquid absorption as well as a dry surface to the wearer are obtained. The absorbent article according to the invention is distinguished by the fact that both of said bodyside liner and said transfer layer contain thermoplastic material and are bonded together in a plurality of bonding sites within which the thermoplastic material has been caused to at least partially soften or melt and thereby bond together the bodyside liner and the transfer layer, wherein the bodyside liner comprises a plurality of perforations and the bonding sites in at least in a central part of the article, corresponding to the so called wetting area, the bonding sites cover an area of between 0.2% and 11% of the total area of said part of the liner that is circumscribed by said bonding sites and that each bonding site has an area of no more than 13 mm$^2$, said liner having a three-dimensional structure of alternating raised and depressed regions, wherein the perforations are present in the bottoms of the depressions of said liner as seen from the body facing side of the liner.

In a further aspect the perforations as a result of the perforation process have edges on the side facing the transfer layer, said edges engaging with the transfer layer to increase the friction between the liner and the transfer layer.

According to another aspect of the invention the three dimensional surface topography of the laminated liner and transfer layer is characterized by any of the following parameters alone or in combination:

Smr(c=150): from 1% to 25%, preferably from 1 to 12%;
Smr(c=200): from 6 to 40%, preferably from 6 to 25%;
Smr(c=500): from 40 to 85%, preferably from 50 and 85%;
Smr(c=750): from 60 to 100%, preferably from 80 to 100%;
Sz: from 700 to 1500 µm, preferably from 800 to 1400 µm;
Sq: from 100 to 300 µm, preferably from 130 to 280 µm;
SΔq: from 0.5 to 0.8;
Sdr: from 10 to 30%, preferably from 15 to 25%;
Sbi: from 0.6 to 0.9;
Sci: from 0.8 to 1.3;
Svi: from 0.1 to 0.15.

According to one embodiment the liner is a nonwoven material, a plastic film or a laminate between at least two nonwoven materials, between a nonwoven material and a plastic film or between a nonwoven material and a wadding.

According to a further embodiment the bonding sites extend in the thickness direction of the transfer layer as well as the liner so as to compress the transfer layer and the liner in the areas of the bonding sites.

In one aspect of the invention the bonding sites are provided by ultrasonic bonding.

The transfer layer is according to one embodiment a porous fibrous material or foam material having a basis weight between 20 and 100 g/m$^2$, preferably between 30 and 80 g/m$^2$.

According to one embodiment the perforated liner is arranged in a longitudinal central area of the article and an edge portion liquid pervious layer is arranged along the longitudinal edge portions of the article and joined to said perforated liner.

It is preferred that the perforated liner has a width in the transverse direction of the article which is at least 50% of the width of the article in the crotch area thereof. It is further preferred that the perforated liner has a width of at least 20 mm, preferably at least 25 mm.

BRIEF DESCRIPTION OF DRAWINGS

The invention will be described in the following in greater detail by way of example and with reference to the accompanying drawings, in which.

DESCRIPTION OF PREFERRED EMBODIMENTS

The invention will in the following be closer described with reference to some embodiments shown in the accompanying drawings.

The term "absorbent article" refers to products that are placed against the skin of the wearer to absorb and contain body exudates, like urine, faeces and menstrual fluid. The invention mainly refers to disposable absorbent articles, which means articles that are not intended to be laundered or otherwise restored or reused as an absorbent article after use.

Figure 1:
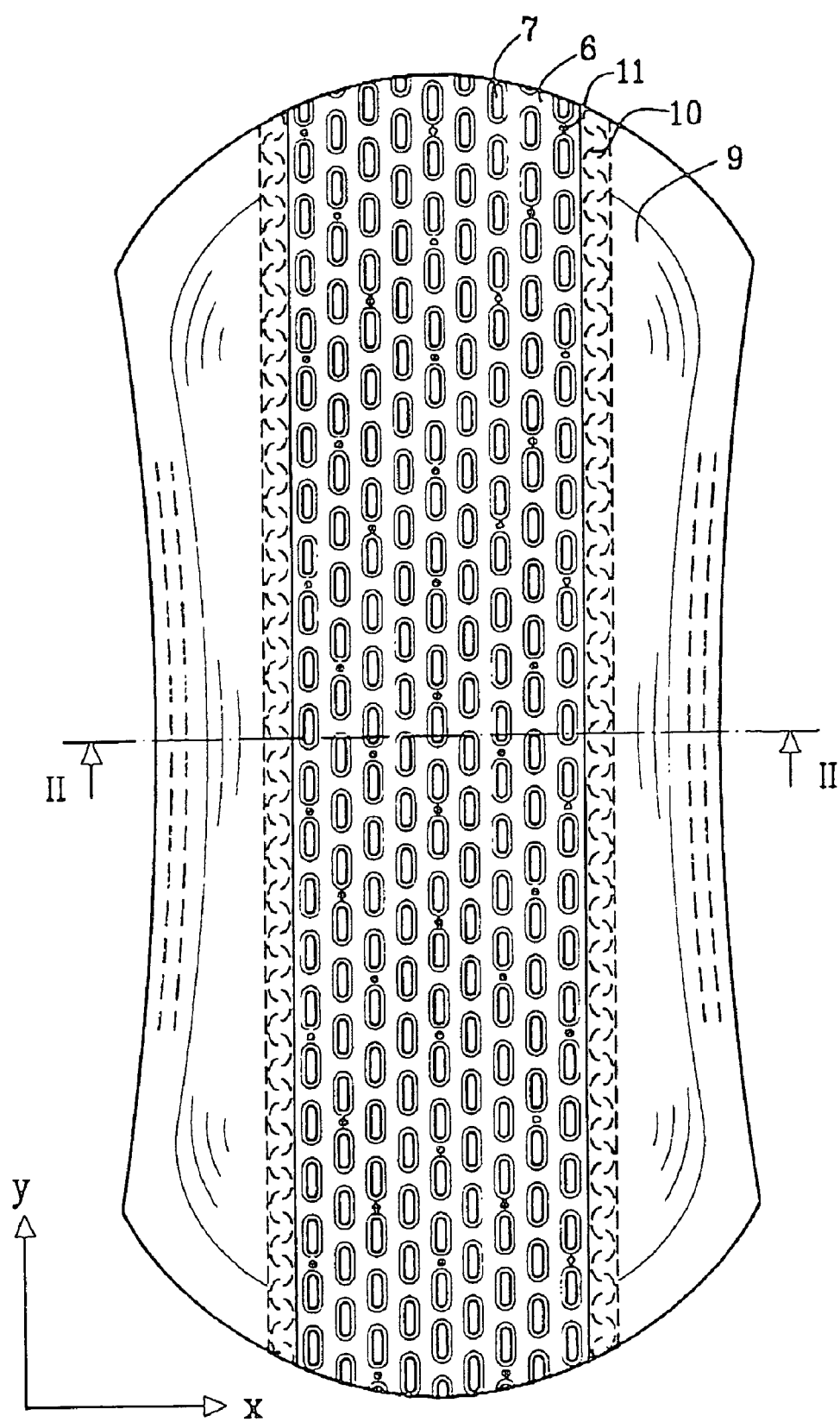
FIG. 1 is a view from above of an absorbent article according to one embodiment of the invention.
Figure 2:
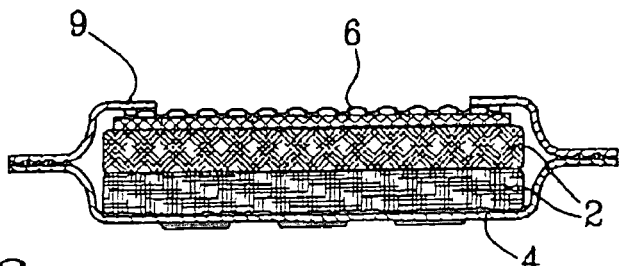
FIG. 2 is a section according to the line II-II in FIG. 1
Figure 3:
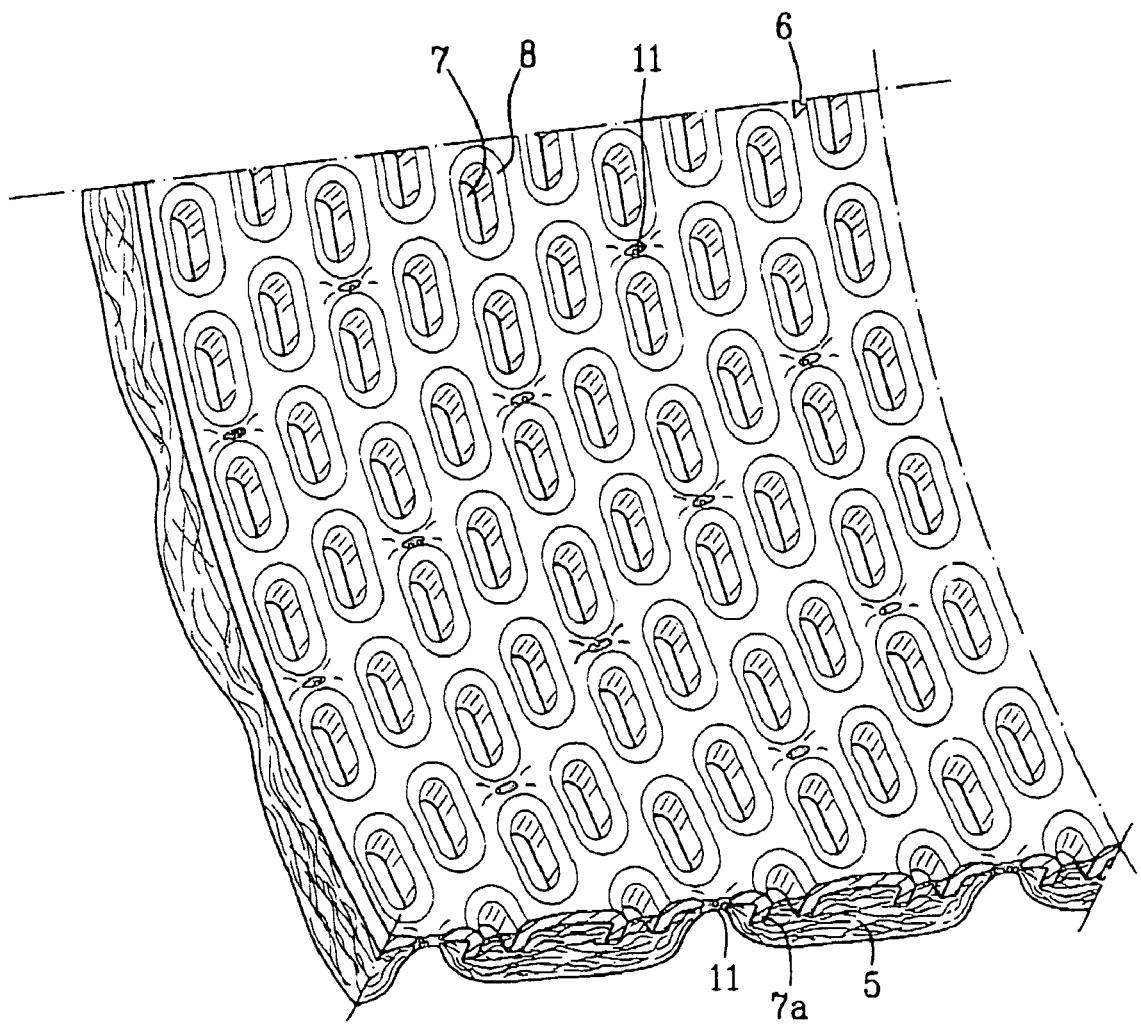
FIG. 3 is a perspective view on an enlarged scale of a laminated liner and liquid transfer layer according to the invention.
Figure 4:
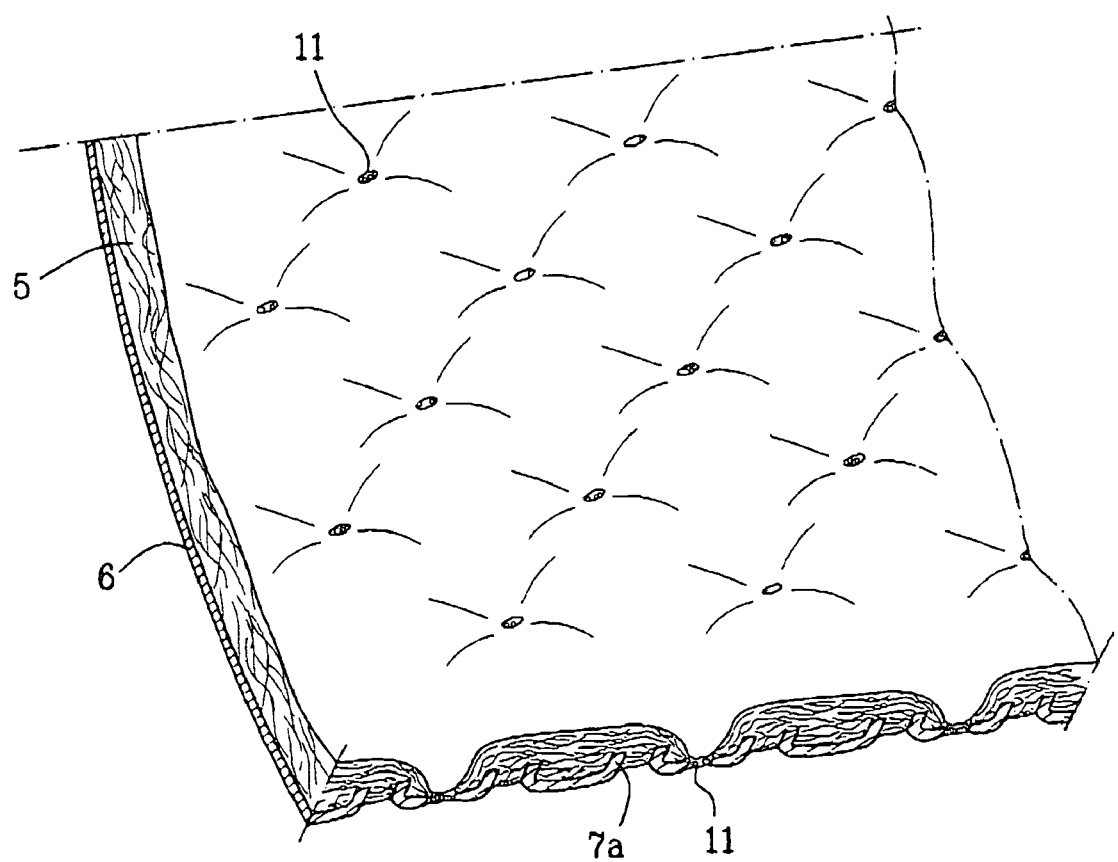
FIG. 4 shows the laminated liner and liquid transfer layer from the side of the liquid transfer layer.
Figure 5:
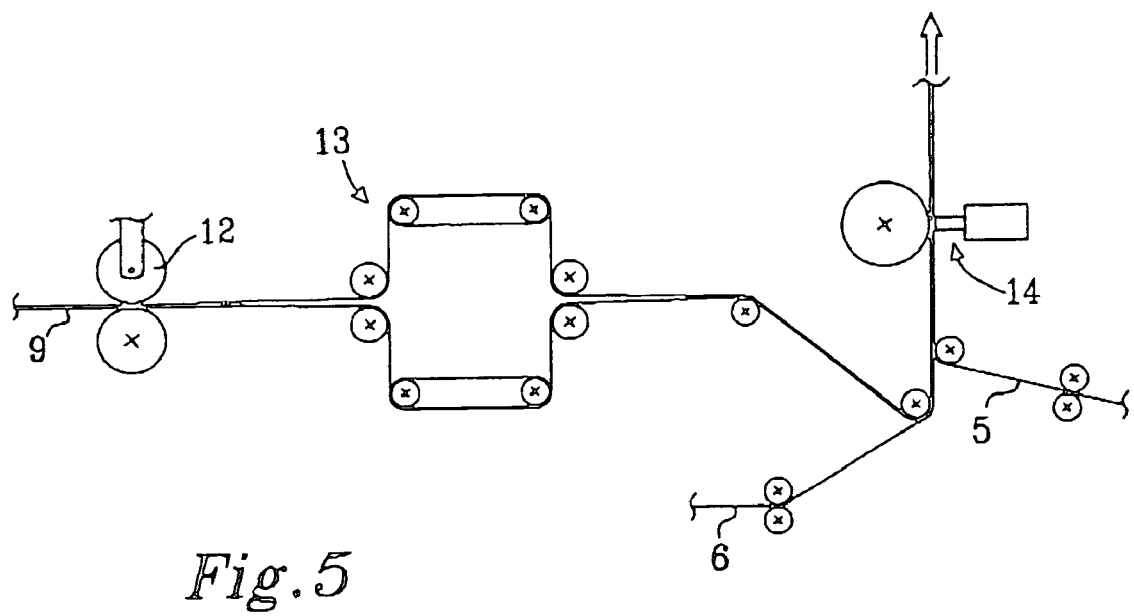
FIG. 5 is a schematic illustration of the manufacturing process for making the laminated liner and transfer layer according to the invention.

The absorbent article shown in FIG. 1 is in the form of an incontinence guard 1. In its most common form the absorbent article comprises an absorbent core 2 and a cover enclosing the absorbent core. Said cover comprises a liquid pervious topsheet 3 on the wearer facing side of the absorbent core 2 and a liquid barrier backsheet material 4 on the garment facing side of the absorbent core.

The topsheet forms the inner cover of the absorbent article and in use is placed in direct contact with the skin of the wearer. The topsheet can comprise a nonwoven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. Further examples of inner liquid permeable cover materials are porous foams, apertured plastic films, laminates between apertured films and nonwovens etc. The materials suited as inner liquid permeable cover materials should be soft and non-irritating to the skin and be readily penetrated by body fluid, e.g. urine or menstrual fluid. The inner liquid permeable cover may further be different in different parts of the absorbent article.

The backsheet material 4 may be a thin plastic film, e.g. a polyethylene or polypropylene film, a nonwoven material coated with a liquid impervious material, a hydrophobic nonwoven material, which resists liquid penetration or a laminate comprising plastic films and nonwoven materials. The backsheet material 4 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens.

The absorbent core 2 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight and in an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent cores comprising layers of different material with different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent core may be varied to be suited for different uses such as for infants or for adult incontinent persons. Other examples of absorption materials useful as absorbent cores are laminates of roll materials, such as airlaid tissue, nonwovens and through-air-dried tissue, and superabsorbent materials, wherein an inner layer or strings of superabsorbent material is present between outer layers of said roll material. The different layers are bonded together by for example glue or by heat bonding.

In the embodiment shown in the drawings the absorbent core 2 comprises two layers, an upper and a lower layer. In other embodiments only one layer or three or more layers may be present.

A liquid transfer layer 5 is arranged between the topsheet 3 and the absorbent core 2. The transfer layer is a porous, resilient, relatively thick material layer, for example in the form of a fibrous wadding, a carded fibrous web, a tow material or other type of bulky and resilient fibrous material having a high momentaneous liquid receiving capacity and which can temporarily store liquid before it is absorbed by the underlying absorbent body. The liquid transfer layer may further be in the form of a porous foam material. It may further consist of two or more material layers. The basis weight of the transfer layer is between 20 and 100 g/m$^2$, preferably between 30 and 80 g/m$^2$.

According to the present invention the topsheet 3 in the central longitudinal (y) region of the article comprises a perforated liquid pervious bodyside liner 6, which may be a nonwoven material, a plastic film or a laminate between at least two nonwoven materials, between a plastic film and a nonwoven material or between a nonwoven material and a wadding material. Perforations 7 are made in the liner 6. The perforations 7 have a length of between 0.5 mm and 5 mm, preferably between 1 mm and 4 mm and a width of between 0.3 and 3 mm, preferably between 0.5 and 2 mm.

The perforation process will result in a three dimensional structure of the liner 6 with the edges 7a of the perforations 7 protruding on the side facing the transfer layer 5, and on the opposite wearer facing side, depressions 8 are formed, wherein the perforations are located in the bottom of said depressions. The protruding edges 7a of the perforations 7 will engage with the underlying transfer layer 5 to increase the friction between the liner 6 and the transfer layer 5.

The topsheet 3 in the longitudinal side edge regions comprises a liquid pervious edge portion liquid pervious layer 9, preferably a soft and smooth fibrous layer. This edge portion layer 9 is joined in an overlapping manner to the perforated liner 6 by gluing, ultrasonic welding or the like. In the drawings an ultrasonic welding pattern joining the central liner 6 and the edge portion layers 9 together is designated with the numeral 10.

The perforated liner 6 preferably has a width in the transverse direction of the article which is at least 50% of the width of the article in the crotch area thereof. It is further preferred that it has a width of at least 20 mm, preferably at least 25 mm. It may cover the entire transverse width of the absorbent core 2 or only the central area thereof. The perforated liner 6 may further extend the entire longitudinal length of the absorbent core 2 or only cover the central region of the absorbent core. It is preferred that it extends over at least 50% of the length of the absorbent core as seen in its longitudinal, y, direction.

In an alternative embodiment the perforated liner 6 constitutes the topsheet of the entire wearer facing side of the article. In such as case perforations 7 may be present in the liner over the entire area thereof or only in the central area of the article.

Part of the topsheet 3 and the backsheet materials 4 extend outward beyond the peripheral edges of the absorbent core 2 and have their inner surfaces bonded to each other, eg by gluing or welding by heat or ultrasonic. In the embodiment shown in FIG. 1, it is the edge portion layer 9 which extends beyond the longitudinal edges of the absorbent core 2 and is bonded to the backsheet material 7, while the perforated liner 6 extends beyond the transverse edges of the absorbent core and is joined to the backsheet material 4. The topsheet 3 and backsheet materials 4 may further be bonded to the absorbent core, e.g. by adhesive.

Both the perforated liner 6 and the transfer layer 5 contain a certain proportion of thermoplastic fibers and are bonded together in a plurality of bonding sites 11 which have been formed by simultaneously compressing the two material layers together and supplying energy thereto. This has caused the thermoplastic material to soften or melt at the bonding sites and thereby bond the two layers 5 and 6 together. The bonding is expediently performed by means of heat bonding or by means of ultrasonic bonding. Thus the bonding sites 11 extend in the thickness direction of the transfer layer 5 as well as the liner 6 so as to compress the transfer layer and the liner in the areas of the bonding sites 11.

The bonding sites 11 are relatively small and each have a size of no more than 13 mm$^2$, preferably between 1 and 8 mm$^2$. The total bonding area is between 0.2 and 11%, preferably between 0.5 and 5%. The total bonding area is defined as the area of the perforated liner that is occupied by the bonding sites 11 in relation to the total area that is circumscribed by the bonding sites. It is herewith pointed out that the bonding pattern 10 joining the perforated liner 6 and the edge portion layers 9 together is not included in the bonding area specified above.

The bonding sites may be regularly distributed over the area of the laminated liner 6 and transfer layer, but they may also be irregularly distributed, for example arranged in groups spaced apart, so that the distance between bonding sites in each individual group is smaller than the distance between adjacent bonding sites in two adjacent groups of bonding sites. The number of bonding sites per unit area should be between 30 and 300 per dm$^2$, preferably between 45 and 190 per dm$^2$. A bonding site 11 may in some cases be composed of a micropattern comprising several small bonding sites on micro scale. However for this purpose it is the bonding sites on a macro scale that are referred to.

The bonding pattern, especially the size of the individual bonding sites 11 and the bonding area are important in order to provide a well balanced interaction between the liner 6 and the liquid transfer layer 5 so that discharged liquid is rapidly absorbed and a soft and dry surface is exposed to the wearer.

In some areas of the perforated liner 6 the bonding pattern could be different to serve another function, for example edge sealing, visual patterns etc. Thus the bonding pattern disclosed above should at least be present in the central part of the article, serving as the so called wetting area. In the peripheral areas of the article the bonding pattern could in alternative embodiments be different. Preferably the bonding pattern according to the invention is present in at least a central third portion of the article as seen in its longitudinal direction, y.

Tests have been performed on eight different bonding patterns. The tested materials were in all other respects equal. The liner 6 was a perforated laminate between a nonwoven material and a plastic film. The perforated laminate had a basis weight of about 40 gsm and was perforated. The perforated laminate was delivered by Tredegar Film Products under the code name X32000. The transfer layer 5 was a nonwoven wadding having a basis weight of 50 gsm. The wadding was delivered by Libletex under the code name T23W.

The liner 6 and the transfer layer 5 were laminated in an ultrasonic welding process with eight different welding patterns. The bonding sites 11 were in all the patterns substantially circular and had a diameter varying between 1.5 mm and 4.0 mm and thus had a size (area) varying from 1.8 mm² to 12.6 mm². The bonding sites 11 were homogeneously distributed over the surface of the laminate and the distance between adjacent bonding sites varied between 4.5 mm and 13 mm, as measured as the shortest distance between the boundary surfaces of adjacent welding points.

The laminates had the following bonding patterns:

TABLE 1

| Sample | Bonding site area (mm²) | Distance between bonding sites (mm) | Bonding area (%) |
|---|---|---|---|
| A | 1.8 | 6 | 1.5 |
| B | 7.1 | 6.5 | |
| C | 7.1 | 4.4 | 10.5 |
| D | 1.8 | 4.5 | |
| E | 1.8 | 10 | 0.83 |
| F | 7.1 | 10 | 3.32 |
| G | 12.6 | 10 | |
| H | 1.8 | 13 | 0.5 |

Sensorial Test

All laminates were tested for softness and surface dryness in a sensorial test. Laminates were placed on a tray, positioned with the centre of the products in the middle of the tray. The samples were compared in pairs (placed in a black box) and the evaluator compared the samples by feeling smoothly on the surface with both hands without pressure and was asked to tell which sample was most rough. No significant differences were found with respect to softness between the eight different laminates. In the surface dryness test the samples were placed on a tray, positioned with the centre of the products in the middle of the tray. The samples were compared in pairs. 80 ml synthetic urine was added with a pump and a cup. After one minute resting the two samples (placed in a black box) the evaluator compared the two samples by feeling smoothly on the surface with both hands without any pressure. The evaluator was asked to tell which sample was most wet. Samples C, D and F were experienced dryer than sample A.

It would be expected that the samples having the more dense bonding patterns would have a dryer surface, which also at least to some extent was shown in the sensorial tests.

Acquisition Time and Rewet

A dosage cup is placed on the centre of the product to be tested and a seal is provided between the product and the dosage cup. A weight of 627 g is applied to the dosage cup. An electronic sensor sensing the presence of liquid is applied against the surface of the sample. 50 ml of synthetic urine is supplied to the dosage cup at a flow rate of 20 ml/sec. The time it takes for the test liquid to be absorbed into the product is registered as Acquisition 1. The cup is removed and the product is let to rest for 10 minutes. The procedure is repeated twice on the same product and with 50 ml test liquid each time, to get the values for Acquisition 2 and 3 respectively.

Reference: Incontinence guard Tena Lady manufactured by SCA Hygiene Products AB having a bodyside liner in the form of a carded nonwoven, 23 gsm, Suominen 650 which was ultrasonically welded to a 50 gsm wadding from Libletex, T23W.

Test sample: In the test sample the bodyside liner was replaced with a perforated laminate as disclosed above. The perforated laminate was ultrasonically welded to the transfer layer in accordance with the present invention.

TABLE 2

| Sample | Acquisition 1 sec. | Acquisition 2 sec. | Acquisition 3 sec. | Rewet g |
|---|---|---|---|---|
| Reference | 9.4 | 17 | 24.2 | 22.6 |
| Test | 5.2 | 6.9 | 10.5 | 13.2 |

A corresponding test performed for all welding patterns A-H showed that the samples with the patterns C and D had a slightly worse acquisition than the others. It is pointed out that the patterns C and D had the largest bonding area.

Kawabata Tests

The Kawabata KES-FB test is a Japanese quality judgment system used for textile materials and is disclosed in "The Standardization and Analysis of Hand Evaluation (2nd Edition), Sueo Kawabata, July 1980, The Hand Evaluation and Standardization Committee, The Textile Machinery Society of Japan". The test used four of the Kawabata testing machines, KES-FB2 for measuring Bending rigidity, B (gf·cm²/cm), KES-FB3 for measuring Compression, EMC (%) and Recovery, RC (%), KES-FB4 for measuring Friction Coefficient, MIU, and KES-FB1 for measuring Shear stiffness, G (gf/cm.degree) and Elongation, EMT (%).

The following Kawabata parameters are then calculated from these measurements according to the below formulas:

Softness (S)

The Softness (S) according to Kawabata is obtained from the formula:

$$S=\sqrt{EMT/B}$$

Drapability (D)

The Drapability (D) according to Kawabata is obtained from the formula:

$$D=116+25\log(B \cdot G/W), \text{ wherein W is the basis weight of the sample.}$$

The following results were obtained:

TABLE 3

| | B, Bending rigidity (gf·cm²/cm) | | | G, Shear stiffness (gf/cm·degree) | | | EMT, Elongation (%) | | |
|---|---|---|---|---|---|---|---|---|---|
| Sample | MD | CD | Mean | MD | CD | Mean | MD | CD | Mean |
| A | 0.245 | 0.186 | 0.216 | 5.33 | 4.72 | 5.02 | 4.31 | 22.90 | 13.61 |
| B | 0.346 | 0.194 | 0.270 | 5.48 | 4.53 | 5.01 | 3.88 | 25.03 | 14.45 |
| C | 0.253 | 0.146 | 0.199 | 6.25 | 5.47 | 5.86 | 3.33 | 21.80 | 12.56 |
| D | 0.299 | 0.174 | 0.236 | 6.29 | 5.25 | 5.77 | 3.49 | 22.10 | 12.80 |
| E | 0.193 | 0.165 | 0.179 | 4.73 | 4.13 | 4.43 | 4.03 | 28.18 | 16.10 |
| F | 0.375 | 0.195 | 0.285 | 4.85 | 4.68 | 4.76 | 4.07 | 23.10 | 13.58 |

TABLE 4

| | MIU, Friction Coefficient | | | SMD, Geometrical surface roughness (μm) | | | EMC, Compression (%) | RC, Recovery (%) |
|---|---|---|---|---|---|---|---|---|
| Sample | MD | CD | Mean | MD | CD | Mean | | |
| A | 0.298 | 0.309 | 0.304 | 2.59 | 4.93 | 3.76 | 58.54 | 47.67 |
| B | 0.290 | 0.308 | 0.299 | 2.63 | 3.44 | 3.04 | 59.95 | 50.17 |
| C | 0.348 | 0.328 | 0.338 | 3.32 | 4.80 | 4.06 | 56.86 | 49.36 |
| D | 0.298 | 0.318 | 0.308 | 4.80 | 4.20 | 4.50 | 57.62 | 51.82 |
| E | 0.335 | 0.300 | 0.317 | 3.31 | 3.86 | 3.58 | 64.59 | 50.97 |
| F | 0.346 | 0.352 | 0.349 | 3.59 | 4.37 | 3.98 | 63.24 | 50.16 |

From these results the Softness (S) and the Drapability (D) according to Kawabata were calculated according to the formulas stated above. The results are stated in Table 5 below.

TABLE 5

| Sample | Softness (S) $\sqrt{EMT/B}$ | Drapability (D) $116 + 25 \log(B \cdot G/W)$ | Basis Weight (W) g/m² |
|---|---|---|---|
| A | 7.94 | 66.4 | 100 |
| B | 7.32 | 71.3 | 96 |
| C | 7.94 | 62.8 | 101 |
| D | 7.36 | 63.6 | 105 |
| E | 9.49 | 62.1 | 96 |
| F | 6.90 | 68.3 | 97 |

The following Kawabata parameters are considered relevant for the purpose of the present invention:

EMC, Compression (%): at least 50, preferably at least 55 and more preferably at least 58%;
RC, Recovery (%): at least 40, preferably at least 45%:
S, Softness: at least 6, preferably at least 7.
MIU, Friction Coefficient: between 0.1 and 0.6 (mean value).

Liner Surface Topography

The surface concept of the present invention is furthermore characterized by its three-dimensional structure. We can show that the surface topography of the liner concept reflects the pattern of the materials and the process parameters in combination. Therefore surface profilometric evaluation and quantification of topography give essential information to which parameters are important to product or material function as well as to the appearance.

The science of profilometry, i.e. where material topography is measured, is well established. This is evident from the extensive standardization of surface parameters and measurement conditions, e.g. DIN EN ISO 4287 which describes $R_a$; Arithmetic mean roughness value. $R_s$ is a well known but seldom significant value of surface roughness, since it provides only very limited information and is insensitive to extreme profile peaks and valleys.

In the following some examples of surface parameters are given, in the text and in references cited. However, it must not be seen as a restricted selection of significant surface parameters, because it is evident that any surface parameter can be shown to have relevance in a given context. Other commonly encountered surface parameters are $R_z$ (maximum roughness profile height), $R_q$ (root mean square roughness value), $R_{sk}$ (skewness), $R_{\Delta q}$ (root mean square profile slope) and $R_{mr(c)}$ (roughness profile material ratio) all of which are covered by the afore mentioned DIN EN ISO 4287 standard. Among other parameters in DIN EN ISO 13 565 are $R_{pk}$ and $R_{vk}$ describing parts of the roughness profile (when filtered out as a material ratio curve, Abbott) corresponding to "peak surface" and "valley surface".

Surface parameters are used to describe cross-sectional (2D) profiles as well as 3D-surfaces. For 3D surface profilometry the same principles as for 2D profilometry are used. To distinguish parameters that are obtained from one cross-sectional measurement (2D) from those obtained from 3D measurements, the latter ones are labelled "S" with an index instead of "R". Otherwise the same indices are used, like e.g. $S_z$ for maximum surface roughness profile height (corresponding to $R_z$ which is maximum roughness profile height).

The 3D surface parameters are described along with the work performed to arrive at standardization equivalent to the DIN EN ISO standards for 2D mentioned above in: Stout, K. J., Sullivan, P. J., Dong, W. P., Mainsah, E., Luo, N., Mathia, T. and Zahyouani, H. The development of methods for the characterisation of roughness in three dimensions, Commission of the European Communities. 1993. (ISBN 0 70441 313 2). The enclosed appendix discloses the 3D surface parameters obtained by the surface measurement system.

Profilometry can be applied to any surface and any material. The choice of measurement technique and instrument will however determine the validity and quality of the results. The properties of the material and the resolution needed will determine which instrument to use. The surface area needed to provide a representative sample must be considered as well as the instrumental precision at the required resolution.

Porous and permeable nonwoven surface materials exhibit e.g. a low reflectance and hence techniques relying on reflectance can be excluded. Furthermore, the variations regarding fiber density of nonwoven or of perforation pattern of polymeric film kinds of materials decide the area of the surface topography measurements. The mentioned types of materials or concepts produced there from can be characterized by profilometry provided a sufficiently large representative area is covered by the technique and instrument of choice.

A number of representative laminated liners and transfer layer covered by the invention were measured with 3D surface profilometry. Samples A, C and F as disclosed above were tested as well as a reference laminate in the form of a carded nonwoven, 23 gsm, Suominen 650 which was ultrasonically welded to a 50 gsm wadding from Libletex, T23W. Two additional samples, A' and A", were also tested, which comprised the same transfer layer and welding pattern as sample A, and a similar perforated liner delivered by Tredegar Film Products under the code name X32000, but from different batches as compared to sample A. In all other aspects samples A, A' and A" are the same.

The instrument which was used rely on optical 3D technique. A description of the technique is found in "Skin Research and Technology", 5, pp. 195-207, 1999: *Rapid in vivo measurement of the topography of human skin by active image triangulation using a digital micro mirror device* by S. Jaspers, H. Hopermann, G. Sauermann, U. Hoppe, R. Lunderstädt and J. Ennen.

For the present invention the following instrumental set up was used:

Instrument: MacroCad (GFMesstechnik GmbH, Teltow/Berlin, Germany)

Measurement method: Projected fringe method

Measurement area: 146 mm*109 mm

Lateral sampling: ca 110 micrometers

Vertical resolution and repeatability: 10 micrometers and 1 micrometers respectively.

Results

TABLE 6

|  | Sa (µm) | Sz (µm) | Sq (µm) | Ssk | SΔq | Sdr (%) | Sbi | Sci | Svi |
|---|---|---|---|---|---|---|---|---|---|
| Lower | 113 | 820 | 135 | −0.96 | 0.59 | 15.1 | 0.69 | 0.84 | 0.09 |
| Upper | 298 | 1726 | 360 | −0.39 | 0.74 | 21.6 | 0.91 | 1.29 | 0.15 |
| Sample A | 176 | 1064 | 204 | −0.46 | 0.62 | 16.1 | 0.73 | 1.22 | 0.11 |
| Sample A' | 201 | 1329 | 246 | −0.89 | 0.74 | 21.6 | 0.83 | 0.99 | 0.14 |
| Sample A" | 258 | 1515 | 309 | −0.93 | 0.60 | 15.2 | 0.89 | 0.93 | 0.14 |
| Sample F | 206 | 1266 | 244 | −0.54 | 0.68 | 18.8 | 0.75 | 1.17 | 0.11 |
| Sample C | 153 | 967 | 178 | −0.21 | 0.59 | 15.0 | 0.65 | 1.38 | 0.09 |
| Reference | 57 | 656 | 76 | −0.34 | 0.61 | 15.8 | 0.62 | 1.41 | 0.13 |

Figure 6:
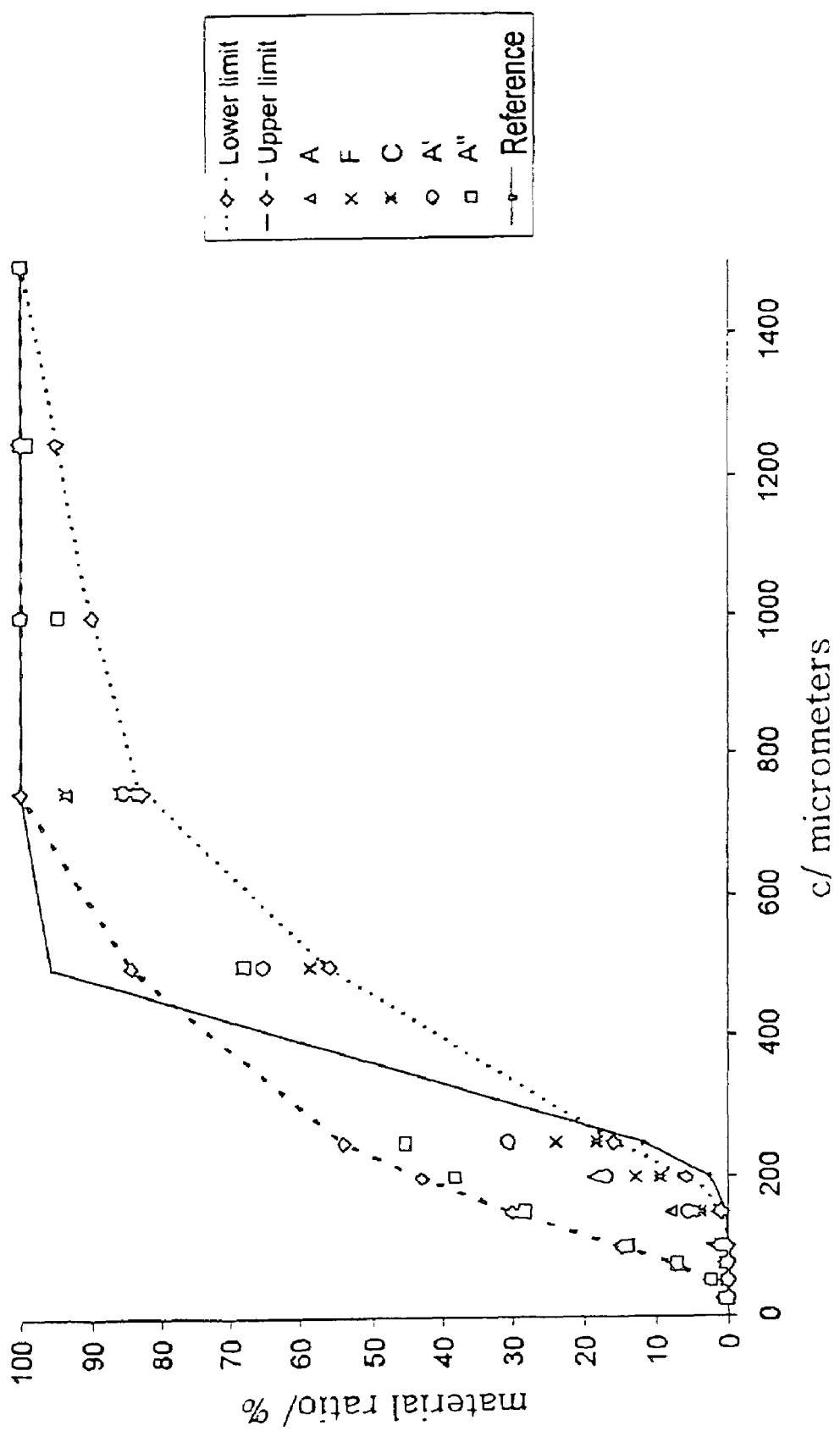
FIG. 6 shows results from topographic measurements illustrating values of Smr(c) with c ranging from 25 to 1500 μm.

The present invention results in a less steep curve for Smr(c)-values from c=25 to c=1500, which is shown in FIG. 6 of the drawings. The values of Smr(c) for the reference concept is represented with a solid line in FIG. 6 whereas Smr(c) series for a laminated liner and transfer layer of the present invention is found around in the area between the dotted lines. While the surface depth of the reference sample is less than 575 µm, the samples according to the invention has a surface depth of more than 1100 µm.

Most modern instruments for surface topography measurements deliver a large number of surface parameters. Among these are the standardized ones and of course also the extensively evaluated 3D parameters discussed and referred to above (Stout, K. J. et al.). In addition instrument manufacturers provide other surface parameters, which are generally accepted because they are logically derived from the standardized 2D parameters or from one of the 3D parameters referred to above (Stout, K. J. et al.).

An example of the latter is C(Smr x %), which is the c-value of Smr(c) (corresponding to Rmr(c) in DIN EN ISO 4287) a parameter quantifying the bearing of the material ratio curve. It is the belief of the inventors that both Smr(c) and C(Smr x %) give relevant information about the liners covered by the present invention. Therefore also some values of C(Smr x %) are given.

TABLE 7

|  | C (Smr = 50%) | C (Smr = 75%) | C (Smr = 100%) |
|---|---|---|---|
| Min cirk | 292 | 444 | 841 |
| Max cirk | 420 | 663 | 1385 |
| Sample A | 361 | 563 | 1084 |
| Sample A' | 356 | 597 | 1367 |
| Sample F | 408 | 648 | 1297 |
| Sample C | 403 | 572 | 989 |
| Reference | 335 | 383 | 687 |

A preferred embodiment of the invention thus can be characterised and distinguished from earlier concept with all of the above surface parameters.

In particular a preferred embodiment of the present invention the laminated liner 6 and transfer layer 5 will be characterized by any of the following 3D surface topography parameters alone or in combination:

Smr(c=150): from 1% to 25%, preferably from 1 to 12%.
Smr(c=200): from 6 to 40%, preferably from 6 to 25%.
Smr(c=500): from 40 to 85%, preferably from 50 and 85%.
Smr(c=750): from 60 to 100%, preferably from 80 to 100%.
Sz: from 700 to 1500 µm, preferably from 800 to 1400 µm.
Sq: from 100 to 300 µm, preferably from 130 to 280 µm.
SΔq: from 0.5 to 0.8.
Sdr: from 10 to 30%, preferably from 15 to 25%.
Sbi: from 0.6 to 0.9.
Sci: from 0.8 to 1.3.
Svi: from 0.1 to 0.15.

Pore Volume Distribution (PVD)

In order to theoretically examine the phenomenon obtained with the welding pattern the pore volume distribution was measured.

The examination included three laminates of combined liners and transfer layers, wherein in one sample (reference) the liner and transfer layers were not combined by welding but just placed on top of each other, and in the two other samples (A and C) the liners and transfer layers were welded together with different welding patterns, see Tables 1 and 8. All three samples were composed of the same liner and transfer layer. The only difference between the samples was the welding pattern.

The separate liner and transfer layers of which the laminates are composed were also tested.

Table 8 gives an overview of the samples.

TABLE 8

| Sample | Material | Bonding area |
|---|---|---|
| Liner | X-32000 from Tredegar film products. Perforated NW/film laminate. | |
| Transfer layer | VTF 142 from Lohman. 50 g/m² | |
| Reference | Laminates of surface material and wadding, described above. | None, the surface material is just placed on top of the wadding. |
| Sample A | Laminates of surface material and wadding, described above. | Bonding site area 1.8 mm² Distance between bonding sites: 6 mm Bonding area: 1.5% |
| Sample C | Laminates of surface material and wadding, described above. | Bonding site area 7.1 mm² Distance between bonding sites: 4.4 mm Bonding area: 10.5% |

The measurements were carried out on aTRI/Autoporosimeter™ with LP992-Liquid Autoporosimeter software, version 1999.2. The AC982, version 1998.2 software was used to process the data for background correction after measurements.

The instrument and softwares are available from TRI/Princeton, 601 Prospect Avenue, P.O. Box 625, Princeton, N.J. 08542.

Following parameter settings was used for the instrument.

| | |
|---|---|
| Sample thickness: | 4 mm |
| Liquid Density: | 0.77 kg/dm3 |
| Surface tension: | 27.6 mN/m |
| COS contact angle: | 1 |
| Chamber height: | 6.4 mm |
| Balance rate: | 2 mg/min |
| Thickness measurement: | Yes |
| Interval: | 30 s |

The liquid used in the measurements was Hexadecane to assure completely wetting of the structure.

The circular samples with a diameter of 50 mm² were taken from the middle of the laminate.

The samples were placed with the liner facing upwards.

Figure 7:
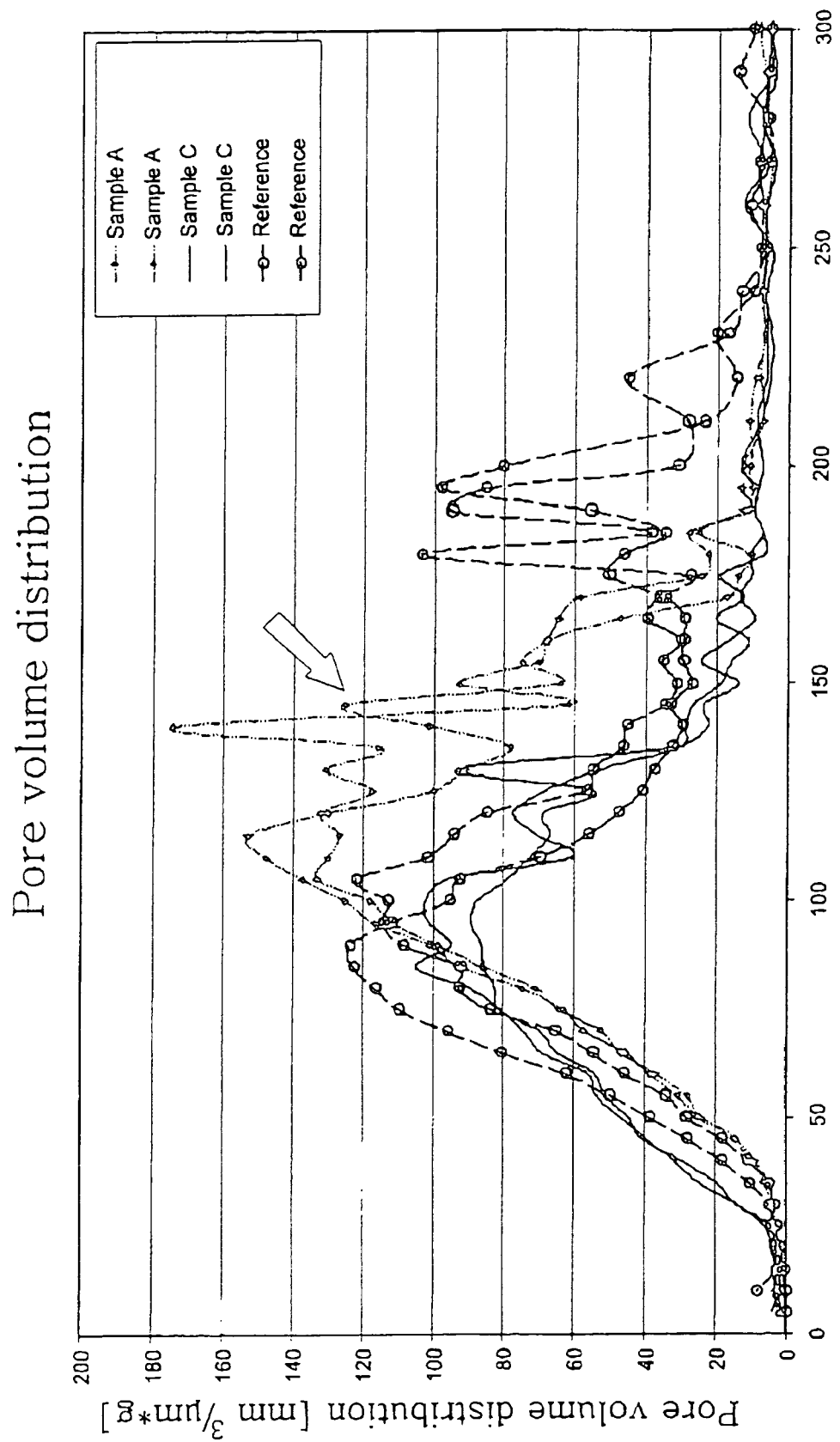
FIG. 7 shows the pore volume distribution (PVD) for some laminated liner and transfer layers.
Figure 8:
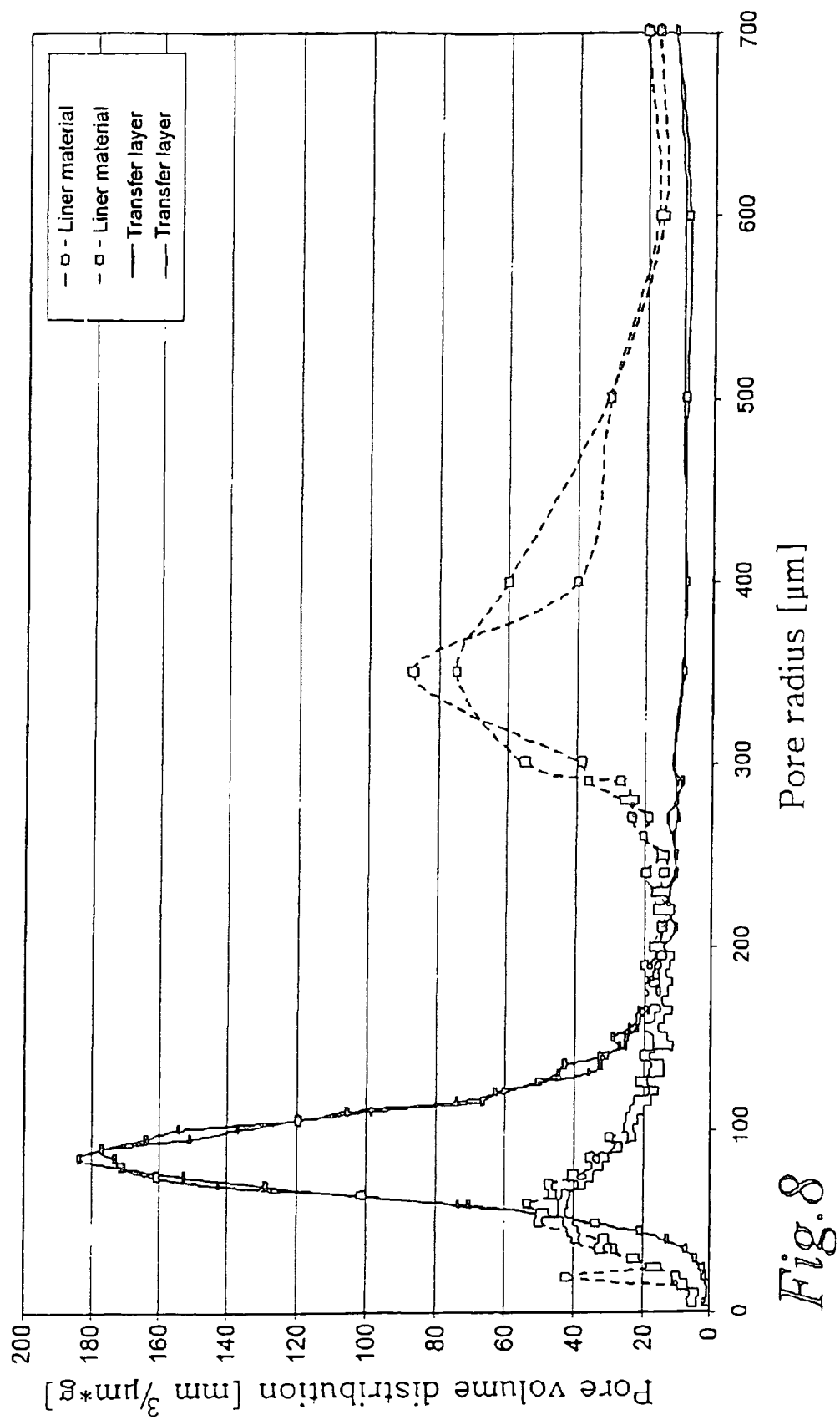
FIG. 8 shows the pore volume distribution (PVD) for the separate liner and transfer layers of which the laminates are composed.
Figure 9:
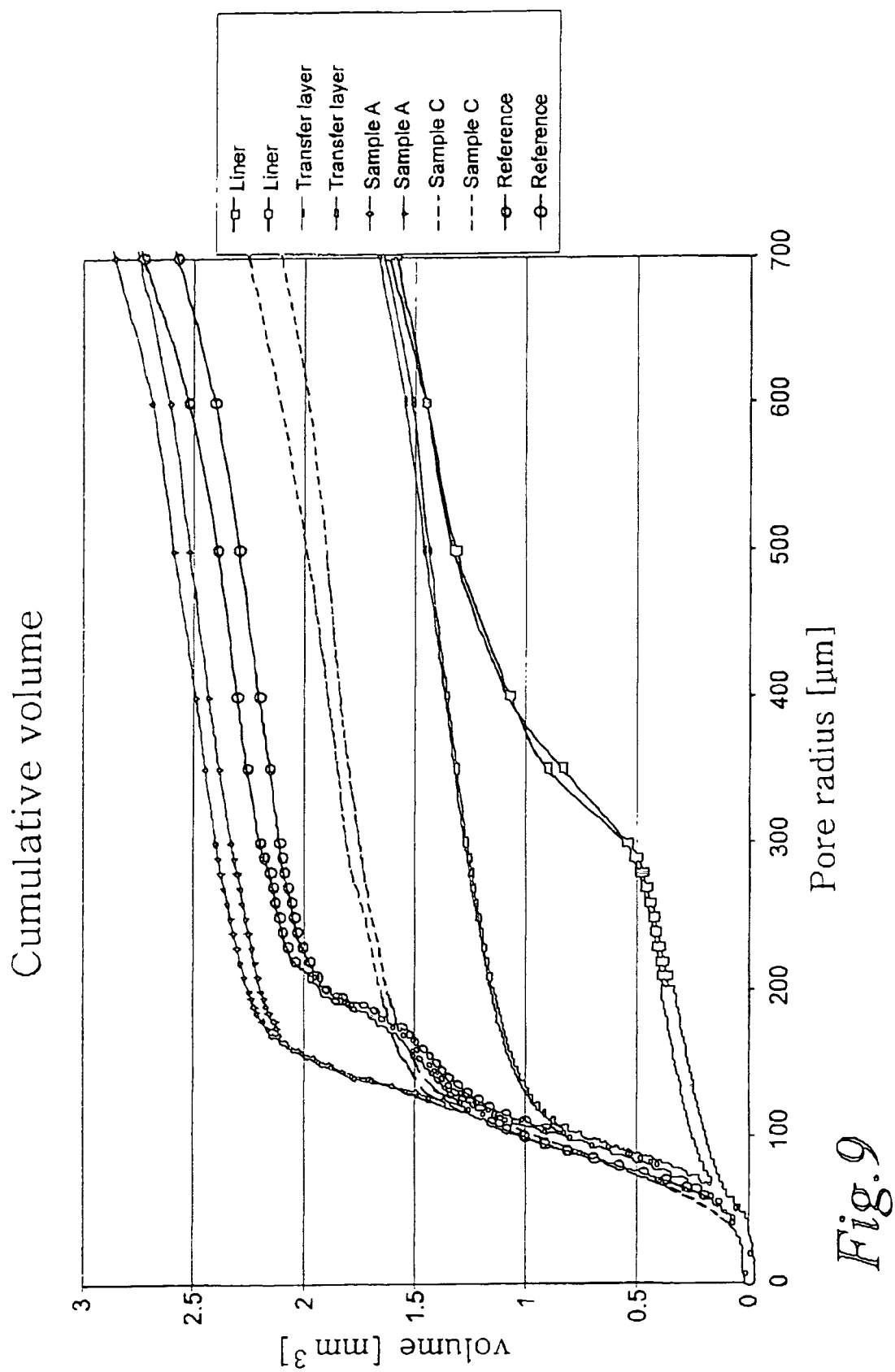
FIG. 9 shows the cumulative volume present in the different samples in FIGS. 7 and 8.

The results obtained are presented in FIGS. 7, 8 and 9, wherein FIG. 7 shows the pore volume distribution (PVD) for the laminates, FIG. 8 shows the pore volume distribution (PVD) for the separate surface and wadding materials of which the laminates are composed. FIG. 9 shows the cumulative volume present in the different samples FIGS. 7 and 8 shows the pore volume distribution of the laminate samples: reference and samples A and C and for the separate liner and transfer layer respectively. The reference and the sample C, which are the unbonded and the densely bonded respectively, have similar distribution of the pore volume for pores between 0 to 300 μm with the exception that the unbonded has a second peak around 200 μm. The pores giving the second peak for the unbonded (reference) are probably inter-layer pores, these pores are removed or made smaller by the welding pattern.

Sample A, having the less dense bonding pattern creates a wide range of pores from 50 to 175 μm. In the interval between 100 and 150 μm sample C has higher amounts of pores than the reference and sample A and than the separate layers (liner and transfer layer respectively).

FIG. 9 shows the cumulative volume present in the different samples and comparing the end volume for the reference sample and sample C it is clear that the bonding pattern compresses the material. However the less dense bonding pattern (sample A) has as much or even more cumulative volume than the unbonded sample (reference), which could have been assumed to have a larger volume. It therefore was surprising that the bonded sample A even had a slightly larger cumulative volume than the unbonded sample (reference). The reason for that is believed to be that a suitable bonding pattern not completely but only pointwise compresses the volume between the two layers so that pores of a relatively large pore size (see the second peak for sample A in FIG. 7 indicated with an arrow) are formed. These pores play an important role for a rapid inlet of liquid. The small pores are important for the rewet properties to keep a dry surface against the wearer.

The combination of a wide range of pore sizes together with the high cumulative volume is believed to be the cause of the good acquisition and rewet properties of the sample A, the laminate with the less dense welding pattern.

Manufacturing Process

A web of edge portion web material 9 is by a slitting knife 12 cut in the middle and is separated in a web separation station 13 to create a gap of a selected width adapted to accommodate the perforated liner 6. The slit web material will form the edge portion liquid pervious layers 9 on opposite longitudinal sides of the perforated liner 6 and is combined with said liner so that it overlaps the edges of the liner 6. A web of transfer layer material 5 is combined with the perforated liner 6 on the opposite side thereof as the edge portion liquid pervious layers 9. In an ultrasonic welding station 14 the different material layers 5, 6 and 9 are combined in a manner disclosed above. Two or more ultrasonic welding stations may be used, for example one for creating the bonding pattern 10 and one for the bonding sites 11. In subsequent steps (not shown) the absorbent core 2 and the backsheet 4 are combined with the process web formed by the perforated liner 6, transfer layer 5 and edge portion liquid pervious layer 9, in order to form the absorbent article. Further components like elastic members or the like may be attached to the article in a suitable manner known in the art.

The invention claimed is:

1. An absorbent article comprising a liquid pervious bodyside liner adapted to be positioned adjacent to a wearer's body, a liquid impervious backsheet and an absorbent core positioned between the bodyside liner and the backsheet, said article further comprising a porous liquid transfer layer between the bodyside liner and the absorbent core, both of said liner and said transfer layer containing thermoplastic material and are bonded together in a plurality of bonding sites within which the thermoplastic material has been caused to at least partially soften or melt and thereby bond together the liner and the transfer layer, said liner comprising a plurality of perforations, said article having a longitudinal direction and a transverse direction, wherein in at least a central part of the article, corresponding to a wetting area, said bonding sites cover an area of between 0.2% and 5% of the total area of said part of the liner that is circumscribed by said bonding sites and that each bonding site has an area of no more than 13 mm², that said liner has a three-dimensional structure of alternating raised and depressed regions and that the perforations are present in the bottoms of the depressions of said liner as seen from the body facing side of the liner, wherein the perforations and the bonding sites are independent from each other and are located at different positions.

2. An absorbent article as claimed in claim 1, wherein each bonding site has an area of no more than 8 mm².

3. An absorbent article as claimed in claim 1, wherein the bonding sites cover an area of between 0.5 and 5%.

4. An absorbent article as claimed in claim 1, wherein the number of bonding sites per unit area be is between 30 and 300 per dm².

5. An absorbent article as claimed in claim 1, wherein the perforations as a result of the perforation process have edges protruding on the side facing the transfer layer, said edges engaging with the transfer layer to increase the friction between the liner and the transfer layer.

6. An absorbent article as claimed in claim 1, wherein the three dimensional surface topography of the laminated liner and transfer layer is comprising any of the following parameters alone or in combination:

Smr(c=150): from 1% to 25%;
Smr(c=200): from 6 to 40%;
Smr(c=500): from 40 to 85%;
Smr(c=750): from 60 to 100%;
Sz: from 700 to 1500 μm;
Sq: from 100 to 300 μm;
SΔq: from 0.5 to 0.8;
Sdr: from 10 to 30%;
Sbi: from 0.6 to 0.9;
Sci: from 0.8 to 1.3;
Svi: from 0.1 to 0.15;
wherein the parameters are determined with a MacroCad (GFMesstechnik GmbH, Teltow/Berlin, Germany) instrument, a measurement method of a Projected fringe method, a measurement area of 146 mm*109 mm, a lateral sampling of ca 110 micrometers, a vertical resolution of 10 micrometers and a vertical repeatability of 1 micrometer.

7. An absorbent article as claims in claim 1, wherein the liner is a nonwoven material, a plastic film or a laminate between at least two nonwoven materials, between a nonwoven material and a plastic film or between a nonwoven material and a wadding.

8. An absorbent article as claimed in claim 1, wherein the bonding sites extend in the thickness direction of the transfer layer as well as the liner so as to compress the transfer layer and the liner in the areas of the bonding sites.

9. An absorbent article as claimed in claim 8, wherein the bonding sites are provided by ultrasonic bonding.

10. An absorbent article as claimed in claim 1, wherein the transfer layer is a porous fibrous material or foam material having a basis weight between 20 and 100 g/m$^2$.

11. An absorbent article as claimed in claim 1, wherein said perforated liner is arranged in a longitudinal central area of the article and that an edge portion liquid pervious layer is arranged along the longitudinal edge portions of the article and joined to said perforated liner.

12. An absorbent article as claimed in claim 11, wherein said perforated liner has a width in the transverse direction of the article which is at least 50% of the width of the article in the crotch area thereof.

13. An absorbent article as claimed in claim 12, wherein said perforated liner has a width of at least 20 mm.

14. An absorbent article as claimed in claim 1, wherein the number of bonding sites per unit area is between 45 and 190 per dm$^2$.

15. An absorbent article as claimed in claim 1, wherein the transfer layer is a porous fibrous material or foam material having a basis weight between 30 and 80 g/m$^2$.

16. An absorbent article as claimed in claim 12, wherein said perforated liner has a width of at least 25 mm.

* * * * *